United States Patent [19]
Minamino et al.

[11] Patent Number: 6,037,452
[45] Date of Patent: Mar. 14, 2000

[54] POLY(ALKYLENE OXIDE)-FACTOR VIII OR FACTOR IX CONJUGATE

[75] Inventors: Hitoshi Minamino, Arcadia; Edward H. Mealey, Fountain Valley, both of Calif.

[73] Assignee: Alpha Therapeutic Corporation, Los Angeles, Calif.

[21] Appl. No.: 07/866,518

[22] Filed: Apr. 10, 1992

[51] Int. Cl.⁷ .................. C07K 14/755; C07K 14/745
[52] U.S. Cl. .................. 530/383; 530/381; 530/384; 530/406; 530/410; 514/21
[58] Field of Search .................. 530/381, 383, 530/384, 410, 406; 515/21

[56] References Cited

PUBLICATIONS

CA(102)2:12355g, Preparation of Blood Coagulation Factor Derivatives, Sep. 29, 1984.

*Primary Examiner*—Michael P. Woodward
*Assistant Examiner*—Stephen Tu
*Attorney, Agent, or Firm*—Sughrue, Mion, Zinn, Macpeak & Seas, PLLC

[57] ABSTRACT

Factor VIIIC:vWF, Factor VIII C, Factor IX or Factor IX or the activated co-factors thereof are covalently linked to a poly(alkylene oxide).

5 Claims, No Drawings

POLY(ALKYLENE OXIDE)-FACTOR VIII OR FACTOR IX CONJUGATE

BACKGROUND OF THE INVENTION

1. Field of the Invention

The present invention relates to non-immunogenic, long acting Factor VIII or Factor IX coagulation factors. The Factor VIII or Factor IX is covalently bonded through a linker or a coupling agent to a poly(alkylene oxide).

2. Description of the Prior Art

Factor VIII and Factor IX are necessary to the human blood coagulation process. Individuals deficient in either Factor VIII or Factor IX usually require administration of the absent coagulation factor on a frequent basis for maintaining a normal blood coagulation profile. These blood proteins are obtained from the blood of donors or prepared using recombinant DNA procedures. At times, more so when obtained from pooled blood, administration of these Factors into the circulatory system can result in an adverse immunogenic response. This can precipitate antibody formation against the administered protein or an allergic response. A second major disadvantage of the currently available Factor VIII and Factor IX formulations is a relatively short half-life, requiring frequent injections.

On the other hand, polyalkylene glycols, especially polyethylene glycol and polypropylene glycol and copolymers thereof (such as Pluronics) have been linked to certain polypeptides to form polyalkylene glycol-polypeptide compounds or conjugates characterized by reduced immunogenicity and prolonged half-life. The specific polypeptides hitherto exemplified in polyalkylene oxide conjugates are distinct in their manner of biological function in comparison with Factor VIII and Factor IX.

In general, Factor VIII and Factor IX are consumed through biochemical conversions during the blood coagulation cascade. This is in contrast to substrates such as enzymes, or hormones which can conform in mating configuration with receptors.

U.S. Pat. No. 4,179,337 to Davis, et al., describes peptide enzymes and peptide hormones coupled to polyethylene glycol or polypropylene glycol of molecular weight 500 to 20,000 daltons to provide physiologically active non-immunogenic water-soluble polypeptide compositions, protected from loss of activity. Enzyme categories of oxidoreductases, tranferases, hydrolases, lyases, isomerases or lipases and the peptide hormones insulin, ACTH, glucagon, somatostatin, somatotropin, thymosin, parathyroid hormone, pigmentary hormones, somatomedin, erythropoietin, luteinizing hormone, chorionic gonadotropin, hypothalamic releasing factors, antidiuretic hormones, thyroid stimulating hormone and prolactin are mentioned. The '337 patent discloses various coupling groups provided by linking or coupling compounds which can link a polyethylene glycol and/or polypropylene glycol to the amino nitrogen or carboxyl carbonyl moiety of the peptide.

On the other hand, Factor VIII and Factor IX are normal plasma proteins which serve as co-factors in the coagulation cascade. Both are large glycoproteins of known amino acid structure. Hemophilia A is associated with Factor VIII deficiency, hemophilia B is associated with Factor IX deficiency.

Unlike true enzymes or intact hormones which illicit their biological activity intact as pure substrates on which activity occurs or in confirmational configuration with receptors, both Factor VIII and Factor IX must undergo cleavage in order to form their active respective co-factors VIIIa and IXa. In the body, serine proteases such as thrombin or Factor Xa activate the inactive co-factors VIII and IX to VIIIa or IXa. Further, Factor VIII circulates in the blood bound to von Willebrand factor. The Factor VIII bound to the von Willebrand factor (Factor VIII:vWF) is designated as Factor VIII:C. The activated co-factor VIIIa or IXa is subsequently inactivated by another serine protease, such as Activated Protein C (APC) or by protease inhibitors.

Thus, each of Factor VIII and IX is consumed in displaying its part in hemostatic process. Indeed, Factor VIII undergoes two cleavages into smaller fragments, the first to provide the active co-factor which participates in the coagulation cascade, and the second to inactivate co-factor. But unlike some biochemical sequences, the inactivation further cleaves the activated co-factors to even smaller proteins.

In contrast, Factor IXa, a protease which is produced from Factor IX by proteolytic removal of a small glycopeptide fragment, rapidly binds antithrombin III in vivo. This complex is removed from circulation by hepatic $\alpha_1$ antitrypsin receptors and thus specifically and rapidly cleared by the liver.

Other prior art describing the linkage of peptides to poly(alkylene oxide) to effect its immunogenicity and/or half-life, is as follows:

U.S. Pat. No. 4,495,285 is directed to the attachment of polyethylene glycol of molecular weight of 200 to 2,000 to amino acid side-chains of plasminogen activators of human origin to improve stability and half-life. All the examples thereof employ urokinase.

U.S. Pat. No. 4,609,546 utilizes as the poly(alkylene-oxide) a polyoxyethylene-polyoxypropylene co-polymer, i.e., methoxy-polyoxyethylene-polyoxypropylene glycol. The peptide can, for example, be a hormone or enzyme. Furthermore, the examples which are mentioned are human menopausal gonadotropin, human growth hormone, epidermal growth factor, nerve growth factor, colony formation stimulating factor, urokinase, plasminogen, kallikrein, interferons, interleukins, urinary trypsin inhibitor, urinary thiol protease inhibitor, placental acylsulfatase, urinary lysozyme and urinary asparaginase. The examples thereof employ urokinase, kallikrein or interferon.

U.S. Pat. No. 4,640,835 is a CIP of U.S. Pat. No. 4,495,285.

U.S. Pat. No. 4,645,741 utilizes lipases and connects them to polyalkylene glycols.

U.S. Pat. No. 4,670,417 bonds hemoglobin via amino groups to poly(alkylene oxide).

U.S. Pat. No. 4,791,192 bonds islet activating protein from biological origin via primary amino groups thereof to polyethylene glycol.

U.S. Pat. No. 4,801,451 employs enzymes while U.S. Pat. No. 4,902,502 and U.S. Pat. No. 5,037,644 employ interleukins. U.S. Pat. No. 5,006,333 employs superoxidase dismutase which is attached via amino, carboxyl or sulfhydryl groups to polyalkylene glycols.

SUMMARY OF THE INVENTION

There are provided by this invention Factor VIII, Factor IX, Factor VIIIa, Factor IXa and analogous polypeptides covalently bonded through a coupling group to poly (alkylene oxide).

It is quite surprising that poly(alkylene oxide) polymers, when covalently bound to Factor VIII and Factor IX, benefit the same. It is expected that an aspect of this benefit results from at least some poly(alkylene oxide) polymer remaining attached to the activated co-factor, while other benefits arise from the linkage of the poly(alkylene oxide) polymer to the inactivated precursor forms, even without retention thereof in the active form. For example, it is currently believed that the active form of Factor VIII (VIIIa) arises from release of large portions of the central connecting regions upon proteolysis of Factor VIII. Since it is known that poly(alkylene oxide) polymer can attach to amino acids along the protein chain, under appropriate conditions, some poly(alkylene oxide) can remain attached to the activated co-factors. Of course, a problem in the use of natural Factor VIII and Factor IX is one of immunogenicity, which is reduced by the presence of the poly(alkylene oxide).

The present invention is not only applicable to Factor VIII and Factor IX obtained from blood, but also to Factor VIII and Factor IX manufactured by recombinant DNA procedures. Further, the present invention is applicable to active Factor VIII and Factor IX fragments (collectively termed Factor VIIIa and Factor IXa since it is believed that Factor VIIIa and Factor IXa can consist of a plurality of different released proteins). Again, these active fragments could be produced by recombinant DNA procedures and, indeed, the complex involved herein can also be prepared by recombinant DNA procedures to provide a poly(alkylene oxide) directly linked to Factor VIII or Factor IX.

Thus, the present invention is not limited to normal Factor VIII (i.e., bound to Factor VIII:vWF) and Factor IX, but also to Factor VIII:C and various active species of any of them, or inactive precursor species (whether of longer or shorter chain length than purified Factor VIII or Factor IX as obtained from blood fractionation).

The Factor VIII and Factor IX, as well as the various activated forms and analogous structures thereof (various analogous structures with deletion, substitution, addition, etc. of one or more amino acids, but retaining the Factor VIII and/or Factor IX biological activity can be prepared, especially through recombinant DNA procedures) as useful herein, should contain an amino terminus and a carboxyl terminus. In addition, linkage along the polypeptide chain or chains forming the same is generally of the amide type as is well known, with some modifications thereof through any intra or inter-chain bonding. Also, as is described in greater detail hereinbelow, bonding of the poly(alkylene oxide) thereto can occur not only at terminal portions of the polypeptide, but also along the chain(s) thereof to form side-chains of poly(alkylene oxide). It is believed that the linking most likely involves formation of covalent bonds using intermediate linking or coupling reagents; however, other types of bond formation are contemplated herein such as ionic bonds, van der Waals force bond, and so forth. Furthermore, the poly(alkylene oxide) can be modified so that only one terminus thereof can participate in the reaction with the peptide (whether or not through a coupling reagent) by preliminarily reacting the poly(alkylene oxide) with an alkyl group such as lower $C_{1-5}$ alkyl, especially methyl or ethyl, to form the corresponding alkoxy groups. Other OH protecting or activating groups can be employed, for example, acyl such as propionyl or other lower acyl ($C_{1-5}$) groups as other protecting groups or, for example, phenyl or alkyl-substituted phenyl groups can be employed. The protecting groups used herein include those known in the art.

Most often, the poly(alkylene oxide) will react through a terminal hydroxyl group (the oxygen) or a modified terminal group such as, for example, when the terminal hydroxyl or hydrogen thereof has been replaced by another reactive moiety such as amino. Of course, the latter is especially useful where reaction is to be with carbonyl moieties of a linker or of the peptide itself.

Known methods of forming an active derivative of the polyalkylene glycol can be employed herein such as the alkylation method, the acid azide method, the diazo method, the condensation method, etc., which are then allowed to react with free amino or carboxyl groups in the peptide to effect bonding.

In the generalized description below, Factor VIII will be exemplified; however, it is understood that Factor IX, Factor VIIIa, Factor IXa, and various analogues thereof can be substituted for Factor VIII.

As the alkylation method, there may be mentioned the method in which the polyalkylene glycol is activated by being led to a triazine derivative or an acetyl derivative. In the following description, P—OH shows the polyalkylene glycol having a hydrophobic group at the other terminal end. E shows a Factor VIII molecule, and the amino group or carboxyl group bonded to E is a free or reactive group in the Factor VIII molecule.

(1) P—OH is allowed to react with cyanuric chloride in the presence of a base in an inert solvent to obtain an active derivative in which one or two P—OH straight chain is bonded. The active derivative is allowed to react with Factor VIII in a buffer to be bonded to the free amino group in Factor VIII

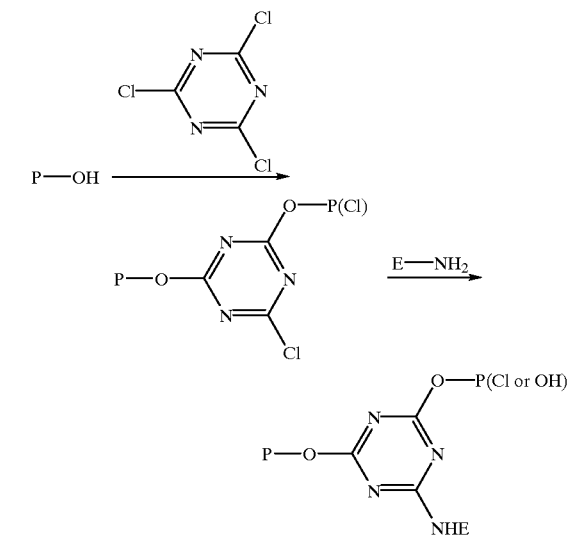

(2) The reaction between P—OH and bromacetyl bromide is carried out in dibromoacetic acid-dioxane to obtain P-bromoacetate. The acetyl derivative is allowed to react with Factor VIII P-dibromosuccinate prepared by use of dibromosuccinic anhydride can also be reacted with Factor VIII.

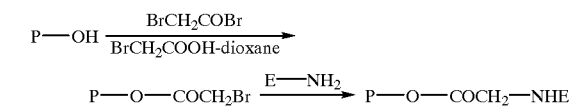

(3) According to the acid azide method, P—OH is allowed to react with chloroacetic anhydride, then with diazomethane to obtain P-acetic acid methyl ether, which is treated with hydrazine to obtain a corresponding hydrazide followed by treatment with sodium nitrite to obtain an acid azide derivative. The active derivative is reacted with Factor VIII to be bonded to free amino groups in Factor VIII.

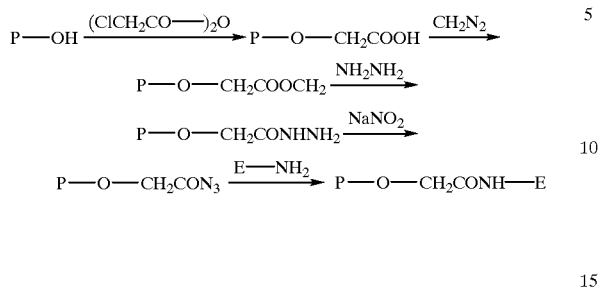

(4) According to the diazo method, for example, P—OH is allowed to react with isatoic acid anhydride to obtain an anthranilic acid ester, which is then treated with sodium nitrite to be converted to a diazonium derivative, followed by diazo-coupling with Factor VIII.

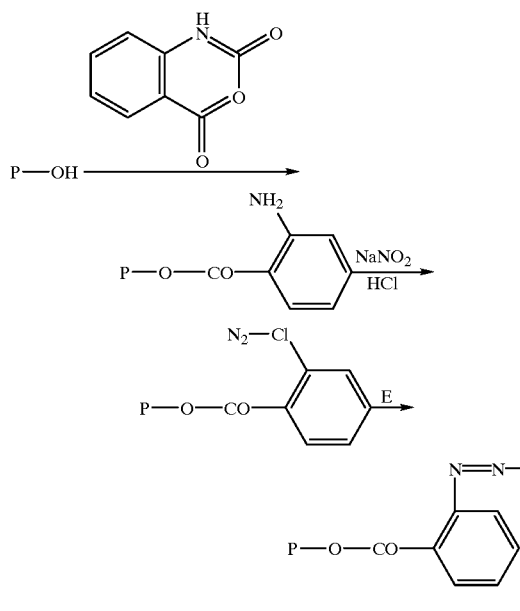

(5) The terminal hydroxyl group of P—OH can be converted to amino group. According to this method, for example, P—OH is allowed to react with tosyl chloride to form P—OH-tosylate, which is then reacted with a phthalimide salt to obtain a N-P-substituted phthalimide, followed by treatment with hydrazine to obtain ω-amino-P—OH. The amino derivative can be directly bonded to carboxyl group in Factor VIII with a carbodiimide reagent or Woodward reagent K. Alternatively, P—OH-tosylate or P—OHω-bromide obtained by the reaction with a halogenating agent may be converted to P—OHω-azide with sodium azide, followed by hydrogen reduction to obtain ω-amino P—OH.

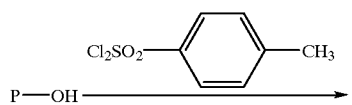

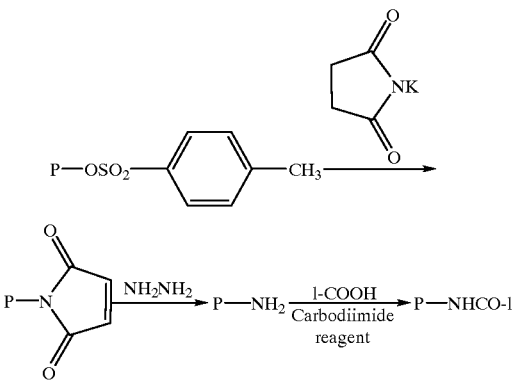

(6) Other than the methods as described above, the carboxylic acid derivative of P—OH can be allowed to react with a bromacetic acid ester in the presence of potassium t-butoxide, followed by hydrolysis, to obtain P-carboxymethyl ether. The carboxylic acid derivative is reacted with N-hydroxysuccinic acid by utilizing a carbodiimide reagent to obtain the corresponding succinimide ester, which is then reacted with amino groups in Factor VIII.

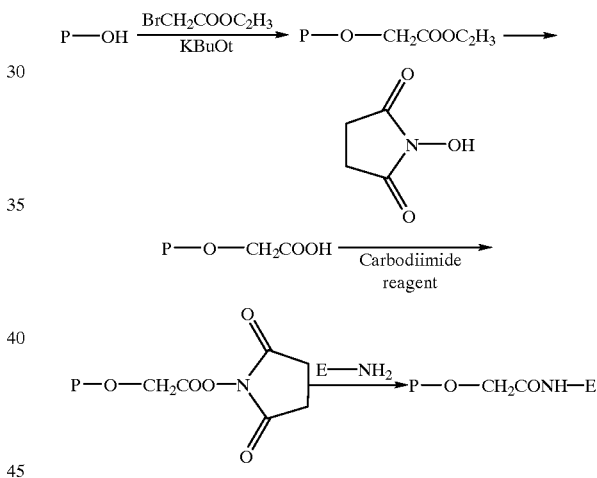

Of the above modified Factor VIII, the modified Factor VIII in which the amino groups of Factor VIII are partially substituted with the groups of the formula:

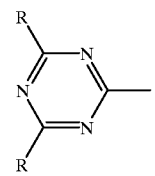

wherein R represents a polyalkylene glycol group having a hydrophobic group at the terminal end is mentioned for the object of the present invention. Mention is also made of modified Factor VIII in which there is substituted 2,4-bis (methoxypolyoxy-ethylene)-6-triazine of which polyoxyethylene moiety has a molecular weight of 5000 or more.

Thus, suitable coupling agents which can be used in the present invention and are adapted to attach a polyalkylene glycol to Factor VIII include those capable of reacting with amino acid side-chains of the protein to be modified in forming chemical bonds therebetween, for example, acyl azide, cyanuric halides, p-diazonium benzyl ether, 3-(p)-diazoniumphenoxy-2-hydroxypropyl ether, dihalogenosuccinic anhydride and the like. The following partial formulae may be given as examples of the coupling structure between the polyalkylene glycol and Factor VIII through these coupling agents, wherein "F" indicates a residual part of the Factor VIII molecule.

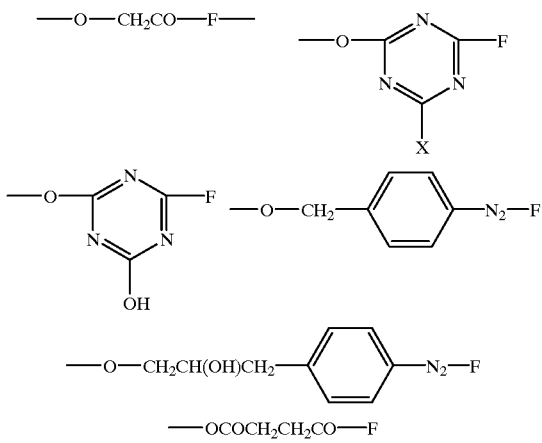

The modified Factor VIII prepared as described above can be purified according to conventional procedures, lyophilized and stored. The percentage of the polyalkylene glycol added to the modified Factor VIII can be measured by determining the unaltered amino groups with trinitrobenzene sulfonic acid, and those containing polyalkylene glycol added to about 50–70% of amino groups in molecules may be structurally useful.

In place of treatment with hydrazine in Method (2) above, there may be utilized N-ethoxycarbonyl-2-ethoxy-1,2-dihydroquinoline (EEDQ). The quinoline is eliminated to give the corresponding mixed carbonic anhydride which is a "disappearing" coupling group having as the effective coupling moiety the methyl carbonyl moiety which attaches itself to free amino groups on the polypeptide to obtain the same type of —OCH$_2$CONH-F structure.

Other known methods of modifying the poly-alkylene glycol can be employed for linkage. For example, the 1-glycydoxy-4-(2'-hydroxy-3'-propyl) butane group can be attached to the terminal oxygen group of the glycol and is reacted with a free amino group of a polypeptide; the carboxyamino or thiocarbonylamino benzyl linkage can be employed, the 2-(hydroxy-3-carboxy)propyl linkage group can be employed, etc.

The polyalkylene glycol is preferably polyethylene glycol, polypropylene glycol or a co-polymer of poly (ethylene oxide) and poly(propyleneoxide), generally of a molecular weight as aforementioned.

The reaction with the peptide is carried out to minimize lose of peptide activity, for example, at temperatures up to room temperature or up to body temperature, say 0 to 98° F., preferably 0 to room temperature, most preferably below room temperature.

The molar ratio between the peptide and the polyalkylene glycol can be regulated to control the degree of substitution of the peptide chain, bearing in mind the length of the peptide chain under consideration. Modification degrees of specific amino acids (where specific amino acids are known to be reacted with specific coupling agents such as reaction of ε-amino groups of lysine with sodium 2,4,6-trinitrobenzene sulfonate) can be determined based on concentration of the coupling agent or modified poly(alkylene oxide) and pH employed in the reaction with the peptide. Various combinations of high pH (about 6.5 to 10) or low pH (about 3.0 to 6.0) with high or low concentration (1.0 to 4.0 molar or 0.1 to 1.0 molar) can provide various degrees of substitution, all of which is quantitatively measured in accordance with conventional analytical techniques, such as mentioned above. The degree of substitution in turn, effects degree of stability where at times extreme stability or half-life may not be desired. Of course, it is also possible to provide a mixture of substituted peptides to provide a sustained release effect where even some peptide is not modified at all for rapid action.

It is believed that at the present times work is undergoing in the art directed to the linkage of polyethylene glycol and/or polypropylene glycol to asparaginase, interferon, superoxide dismutase, adenosine deaminase (this has been recently approved by the FDA), hemoglobin, colony stimulating factor, antibodies, catalase, uricase or monoclonal antibodies.

The following examples are set forth to illustrate the present invention.

EXAMPLE 1

Factor VIII obtained from pooled blood plasma (consisting of human Factor VIII:C bound to von Willebrand's Factor VIIIC.vWF plus minor impurities including fibrinogen and fibronectin) following fractionation and purification is reacted with activated polyethylene glycol and Factor VIIIC:vWF (10–100 Iu/ml). The pH of the reaction is maintained around 8.5 under buffered conditions. The buffer also contains 2 mm potassium thiocyanate (KSCN). The reaction is allowed to proceed up to 48 hours at 4 to 6° C. After completion of the reaction, the unreacted polyethylene glycol is removed by dialysis against an appropriate buffer (i.e., 25 mm histidine containing 0.1 m arginine; pH 7.3). The PEG-coupled Factor VIIIC.vWF is then assayed for activity and stored frozen or lyophilized.

EXAMPLE 2

The above Example is repeated using Factor IX obtained from donors instead of Factor VIIIC:vWF.

EXAMPLE 3

Above Example 1 is repeated using Factor VIII:C in place of Factor VIIIC:vWF.

EXAMPLE 4

Above Example 1 is repeated using Factor VIIIa in place of Factor VIIIC:vWF.

EXAMPLE 5

Above Example 1 is repeated using Factor IXa in place of Factor VIIIC:vWF.

We claim:

1. A covalently bonded conjugate comprising Factor VIII C:vWF coupled to a poly(alkylene oxide) through -carbonyl- groups of said Factor VIII C:vWF.

2. A covalently bonded conjugate comprising Factor IX coupled to a poly(alkylene oxide) through -carbonyl- groups of said Factor IX.

3. A covalently bonded conjugate comprising Factor VIII:C coupled to a poly(alkylene oxide) through -carbonyl- groups of said Factor VIII:C.

4. A covalently bonded conjugate comprising Factor VIIIa coupled to a poly(alkylene oxide) through -carbonyl- groups of said Factor VIIIa.

5. A covalently bonded conjugate comprising Factor IXa coupled to a poly(alkylene oxide) through -carbonyl- groups of said Factor IXa.

* * * * *